United States Patent [19]

Schurter et al.

[11] 4,213,774
[45] Jul. 22, 1980

[54] PYRIDYLOXY-PHENOXY-α-PROPIONIC ACID AMINOALKYL ESTERS

[75] Inventors: Rolf Schurter; Hermann Rempfler; Beat Böhner, all of Binningen, Switzerland

[73] Assignee: Ciba-Geigy Corporation, Ardsley, N.Y.

[21] Appl. No.: 5,538

[22] Filed: Jan. 22, 1979

[30] Foreign Application Priority Data

Jan. 27, 1978 [CH] Switzerland .......................... 928/78

[51] Int. Cl.² .................... C07D 213/64; A01N 9/22
[52] U.S. Cl. ........................................... 71/94; 71/90;
71/92; 546/261; 546/295; 546/276; 546/275;
546/278; 546/279; 546/280; 546/281; 546/294;
544/55; 544/60; 544/124
[58] Field of Search ............... 546/261, 295, 276, 275,
546/278, 279, 280, 281, 294; 544/55, 60, 124

[56] References Cited

U.S. PATENT DOCUMENTS

| | | | |
|---|---|---|---|
| 1,134,751 | 1/1979 | Nishiyama et al. | 546/261 |
| 4,083,714 | 4/1978 | Takahashi et al. | 546/261 |
| 4,092,151 | 5/1978 | Takahashi et al. | 546/261 |
| 4,115,102 | 9/1978 | Takahashi et al. | 546/261 |
| 4,133,675 | 1/1979 | Schurter et al. | 546/275 |

*Primary Examiner*—John M. Ford
*Attorney, Agent, or Firm*—Harry Falber

[57] ABSTRACT

Pridyloxy-phenoxy-propionic acid-amino-alkyl esters having a herbicidal action, their production, compositions containing them, and the use thereof are described. The esters correspond to the formula

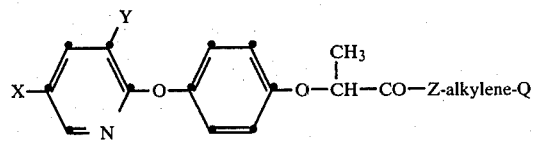

in which
X is halogen or trifluoromethyl,
Y is hydrogen, halogen or trifluoromethyl,
Z is oxygen or sulfur,
"alkylene" is a straight-chain or branched-chain $C_2$–$C_6$ alkyl group, and
Q is an amino or ammonium group.

10 Claims, No Drawings

PYRIDYLOXY-PHENOXY-α-PROPIONIC ACID AMINOALKYL ESTERS

The present invention relates to novel pyridyloxy-phenoxy-α-propionic acid-aminoalkyl esters which are effective as herbicides and as agents regulating plant growth, to processes for producing them, to compositions containing them as active substances, and to the use of these esters, or of compositions containing them, as herbicides or as regulators of plant growth.

The pyridyloxy-phenoxy-propionic acid-aminoalkyl esters are novel compounds and they correspond to the formula

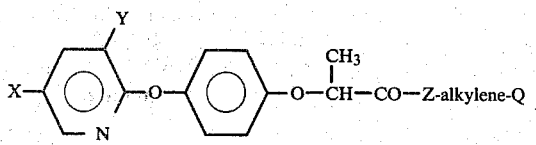

in which
X is a halogen atom or the trifluoromethyl group,
Y is hydrogen, a halogen atom or the trifluoromethyl group,
Z is oxygen or sulfur,
"alkylene" is a straight-chain or branched-chain $C_2$–$C_6$ alkyl group which can be interrupted by oxygen,
Q is an amino or ammonio group

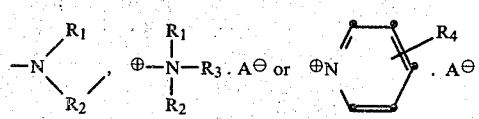

$R_1$ is hydrogen, $C_1$–$C_6$ alkyl unsubstituted or substituted by hydroxyl, halogen, cyano, $C_1$–$C_4$ alkoxy, carboxyl or $C_1$–$C_4$ alkoxycarbonyl, or it is $C_3$–$C_6$ alkenyl unsubstituted or substituted by halogen, or it is $C_3$–$C_6$ alkynyl,
$R_2$ is the same as $R_1$ or it is phenyl unsubstituted or substituted by halogen, $C_1$–$C_4$ alkyl, $C_1$–$C_4$ alkoxy, $C_1$–$C_4$ alkylthio, cyano, nitro or trifluoromethyl,
$R_1$ and $R_2$ together with the nitrogen atom to which they are bound are also a 5–6-membered heterocycle which can contain as second hetero atom oxygen, sulfur or nitrogen, and can be substituted by $C_1$–$C_4$ alkyl or phenyl,
$R_3$ is the same as $R_1$,
$R_4$ is hydrogen, methyl, ethyl or halogen, and
$A^\ominus$ is the anion of an organic or inorganic acid.

The halogen atoms in the above formula are preferably chlorine or bromine. The alkyl or alkenyl groups contain the given number of carbon atoms and can be branched-chain or straight-chain. Preferred as alkenyl groups are the optionally chlorinated allyl and methallyl group; the preferred alkynyl group is the propargyl group. The 5–6-membered heterocycles Q, which are formed by the radicals $R_1$ and $R_2$ together with the nitrogen atom to which they are bound, are preferably the pyrrol, pyrrolidine, pyridine, piperidine, morpholine, thiomorpholine as well as the piperazine ring. These rings can be substituted by a $C_1$–$C_4$ alkyl group, preferably methyl; the piperazine group can also be substituted by phenyl.

Phenoxy-phenoxy-propionic acid esters and pyridyloxyphenoxy-propionic acid esters having a similar chemical structure have become known from new publications (see German Offenlegungsschriften Nos. 2,546,251, 2,617,804 and 2,623,558).

The active substances of the formula I according to the invention and the herbicidal compositions containing them as active ingredients are particularly suitable for selectively combating difficultly controllable wild grasses in crops of cultivated plants, also in crops of cultivated monocotyledonous plants, such as wheat and other varieties of cereals. The compounds according to the invention are thus excellently compatible with cultivated plants, such as wheat, and very effective against wild grasses.

The phenoxy-phenoxy-alkanecarboxylic acid esters substituted in the ester side chain by the amino or ammonio group, which are already known from the prior art, such as the already mentioned esters and thioesters of German Offenlegungsschriften Nos. 2,617,804 and 2,623,558, respectively, are either too aggressive towards sensitive cultivated plants, for example wheat, or, with good compatibility with cultivated plants, too mild in their action against the wild grasses to be combated.

Compared to the said known compounds, the active substances according to the invention are distinguished by clearly better compatibility with cultivated plants, such as wheat in particular (selectivity), and at the same time better activity against wild grasses, especially such as *Avena fatua* (wild oats).

The object of this invention is therefore to provide novel derivatives of the class comprising 4-(pyridyloxy)-α-phenoxy-propionic acids and 4-(pyridyloxy)-α-phenoxy-thiopropionic acids, which are in their herbicidal action against wild grasses difficult to control superior to known compounds of similar structure, and more compatible than these with important cultivated plants, such as wheat, and they thus constitute an enlargement of the prior art.

Processes known per se are used to produce the novel esters of the formula I.

One of these processes comprises reacting a corresponding 4-(3′,5′-dihalogenopyridyl-(2′)-oxy)-α-phenoxy-propionic acid halide of the formula II

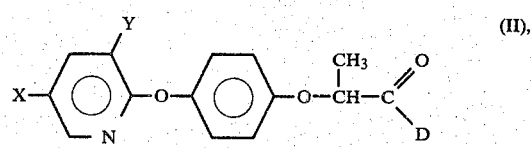

in which X and Y are as defined under the formula I, and "D" is a halogen atom or a reactive ester radical, in the presence of a basic acid acceptor, with an alcohol or thiol of the formula III

in which "alkylene", Q and Z are as defined under the formula I.

A further process comprises reacting the corresponding hydroxy-phenyl-pyridyl ether, or a salt thereof, of the formula IV

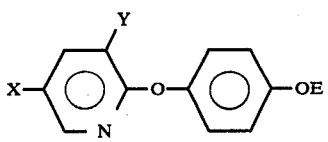 (IV), in which X and Y are as defined under the formula I, and E is hydrogen or the equivalent of an alkali metal cation or alkaline-earth metal cation, with an α-halogenopropionic(thiol)acid ester of the formula V

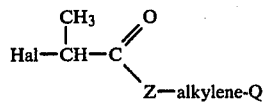 (V), in the presence of an acid-binding agent (base). In these formulae, "alkylene", "Hal", Q and Z are as defined under the formula I.

Finally, the compounds of the formula I can be produced, likewise in a known manner, by reacting a compound of the formula VI

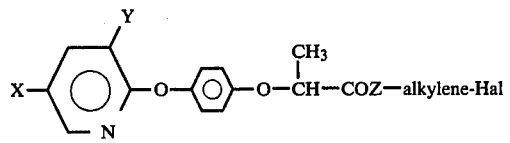 (VI), in which "alkylene", X, Y and Z are as defined under the formula I, whilst "Hal" is a halogen atom, with an amine of the formula VII

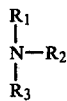 (VII), in which $R_1$, $R_2$ and $R_3$ are as defined under the formula I.

Quaternary ammonium compounds can also be produced by reacting a compound of the formula I, in which Q is the amino group

, with a compound of the formula VIII

A—$R_3$ (VIII)

in the customary manner. In these formulae, $R_1$, $R_2$, $R_3$ and A are as defined under the formula I.

These reactions are performed in solvents under normal pressure, or in a pressure vessel at 0°–180° C., preferably at 20°–150° C. In order to accelerate the reaction, the reaction mixture can be heated to the boiling point of the solvent.

The reactions are preferably performed in a solvent which is inert to the reactants. Suitable solvents are solvents from the widest variety of classes of substances, such as aliphatic and aromatic, optionally chlorinated hydrocarbons, for example ethylene chloride, etc., and also polar organic solvents, such as alcohols, ethers, ketones, amides, stable esters, for example methyl ethyl ketone, dimethoxyethane, dimethylformamide, dimethylsulfoxide, tetrahydrofuran, and so forth.

As basic acid acceptors for the reaction with the halogen compounds of the formulae II and V, it is possible to use aqueous alkali metal hydroxides, such as KOH and NaOH, as well as further customary basic substances, such as carbonates ($K_2CO_3$, $NaHCO_3$), alcoholates ($NaOCH_3$ and potassium-tert-butylate), and also organic bases, such as triethylamine, and others.

The starting materials of the formulae II to V are in some cases known, or they can be produced by known processes.

The propionic acid thiol esters of the formula I (Z=sulfur) can be obtained also by reacting the corresponding free 4-(pyridyl-(2')-oxy)-α-phenoxy-thiopropionic acid, or a metal salt of this acid, with an aminoalkyl halide of the formula Hal-alkylene-Q in the presence of a base.

The above-mentioned free thiopropionic acid and metal salts thereof, and also the production thereof from the corresponding propionic acid halide with hydrogen sulfide, $Na_2S$ or NaHS, in the presence of a basic acid acceptor, is the subject matter of a pending patent application. The 4-(3',5'-dichloropyridyl-(2')-oxy)-α-phenoxy-thiopropionic acid produced by this method is an oil having a refractive index $n_D^{21}=1.5787$, which melts at 85°–87° C. after recrystallisation.

The Examples which follow illustrate the production of some active substances of the formula I according to the invention. Other final products of the formula I which are produced in a corresponding manner, or by another of the methods mentioned in the text, are subsequently listed in tabular form.

EXAMPLE 1

α-[4-(3',5'-dichloropyridyl-2'-oxy)-phenoxy]-propionic acid-dimethylaminoethyl ester

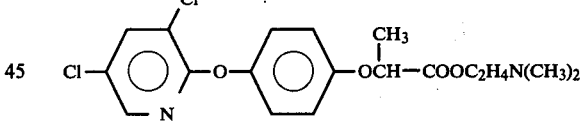

(a) 51.9 g (0.15 mol) of α-[4-(3',5'-dichloropyridyl-2'-oxy)-phenoxy]-propionic acid chloride is added dropwise at room temperature to a mixture of 15.0 g (0.165 mol) of 2-dimethylaminoethanol, 22.9 ml (0.165 mol) of triethylamine and 300 ml of methylene chloride. The temperature is meanwhile allowed to rise to 35° C. After 1 hour's stirring, 100 ml of water is added and the mixture is thoroughly stirred. The organic phase is filtered directly through a small silica gel column. The filtrate is concentrated by evaporation to obtain 55.3 g (92.3% of theory) of the above product in the form of clear yellow oil having a refractive index of $n_D^{20}=1.5498$.

The acid chloride required as starting material is produced as follows:

(b) 30 ml of thionyl chloride is added to 26.8 g (0.082 mol) of α-(4-(3',5'-dichloropyridyl-2'-oxy)-phenoxy)-propionic acid, and, after the evolution of gas has subsided, the temperature is raised to 50° C. After 2 hours, the reaction mixture is concentrated in vacuo; 100 ml of toluene is then added and the whole is again concentrated by evaporation. The product obtained is a dark-brown oil, which slowly commences to crystallise. The yield is 25.9 g (86.7% of theory) of α-(4-(3',5'-dichloropyridyl-2'-oxy)-phenoxy)-propionic acid chloride having a melting point of 45° C.

EXAMPLE 2

α-[4-(3',5'-dichloropyridyl-2'-oxy)-phenoxy]-thiopropionic acid-S-diethylaminoethyl ester

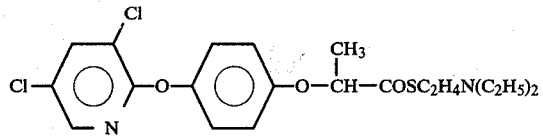

(a) 16.0 g (0.046 mol) of α-[4-(3',5'-dichloropyridyl-2'-oxy)-phenoxy]-thiopropionic acid is dissolved in 50 ml of methyl ethyl ketone, and to the solution at room temperature is added 14.4 g (0.104 mol) of potassium carbonate. The temperature rises to 28° C. as a result of the exothermic reaction. After 30 minutes, 8.6 g (0.05 mol) of 2-diethylaminoethyl chloride.HCl is added, whereupon the temperature rapidly rises to 40° C., and the reaction mixture is stirred at this temperature for 1 hour. It is then filtered off directly through a small silica gel column. The filtrate is concentrated by evaporation to obtain, as a clear yellow oil, 8.6 g (42.2% of theory) of the above product having the refractive index $n_D^{20} = 1.5616$.

The thiopropionic acid used as starting material is produced as follows:

17.2 g (0.0496 mol) of α-(4-(3',5'-dichloropyridyl-2'-oxy)-phenoxy)-propionic acid chloride, produced according to Example 1b, is added dropwise to a mixture of 8.9 g of KOH in 4.9 ml of water and 75 ml of dimethoxyethane which has been saturated at 10°–15° C. with H₂S with vigorous stirring. During the dropwise addition, the temperature is held at 10° C. with an ice bath. The reaction mixture is subsequently stirred for 30 minutes at room temperature, and is then poured into 150 ml of ice/water. The cloudy brown solution is adjusted to pH 1 with concentrated HCl, in the course of which there precipitates a brown oil, which is taken up in methylene chloride. The organic phase is put directly through a small silica gel column, and rinsed well with methylene chloride. The light-yellow solution is concentrated by evaporation to obtain a clear orange oil, which crystallises on trituration with petroleum ether. There is obtained 16.8 g of α-(4-(3',5'-dichloropyridyl-2'-oxy)-phenoxy)-thiopropionic acid in the form of yellow crystals having a melting point of 85°–87° C.

EXAMPLE 3

α-[4-(3',5'-dichloropyridyl-2'-oxy)-phenoxy]-thiopropionic acid-S-(2-diethylmethyl-ammonium)-ethyl ester iodide

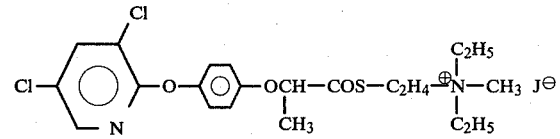

20 ml of methyl iodide is added at room temperature to 4.6 g (0.0104 mol) of the α-[4-(3',5'-dichloropyridyl-2'-oxy)-phenoxy)]-thiopropionic acid-S-(2-diethylamino)-ethyl ester obtained according to Example 2. The reaction mixture is heated at 35° C. for 10 minutes; it is subsequently concentrated in vacuo to leave a solid residue, and this is triturated with a small amount of ether. On filtration and drying, there is obtained 4.2 g (70%) of theory of the above product in the form of a yellow crystalline powder having a melting point of 80° C.

EXAMPLE 4

α-[4-(3',5'-dichloropyrid-2'-yloxy)-phenoxy]-propionic acid-2-N-piperidinoethyl ester

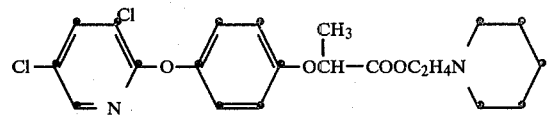

(a) 15.2 g (0.035 mol) of α-[4-(3',5'-dichloropyridyl-2'-oxy)-phenoxy]-propionic acid-2-bromoethyl ester together with 10 ml of toluene and 7.4 ml (0.075 mol) of piperidine are heated to 100° C., in the course of which all constituents go into solution, and the thin-layer chromatogram shows that after 2 hours no further starting material is present. The reaction mixture is diluted with a small amount of ethyl acetate, and washed with water. The organic phase is dried with sodium sulfate and concentrated by evaporation to thus obtain 13.2 g (85.7% of theory) of the title product having a refractive index of $n_D^{21} = 1.5448$.

The starting product is produced as follows:

(b) 173.0 g (0.5 mol) of α-(3',5'-dichloropyridyl-2'-oxy)-phenoxy)-propionic acid chloride is added dropwise at 10° C. to a mixture of 39 ml (0.55 mol) of ethylene bromohydrin and 76 ml (0.55 mol) of triethylamine in 300 ml of toluene, and the reaction is slightly exothermic. No further starting material is found in the thin-layer chromatogram after 10 minutes' stirring. The reaction mixture is washed with a small amount of water; and the organic phase is then dried with sodium sulfate and concentrated by evaporation to leave as residue a clear yellow oil, which on trituration with petroleum ether forms white crystals. The yield is 181 g (83.4% of theory) of α-(4-(3',5'-dichloropyridyl-2'-oxy)-phenoxy)-propionic acid-2-bromoethyl ester having a melting point of 106°–107° C.

$$X-\underset{N}{\underset{|}{\bigcirc}}-O-\bigcirc-O-\underset{CH_3}{\underset{|}{CH}}-COZ \text{ alkylene Q}$$

with Y substituent on the pyridine ring.

| No. | X | Y | —Z-alkylene Q | Physical constants |
|---|---|---|---|---|
| 1 | Cl | Cl | $-O-C_2H_4N(CH_3)_2$ | $n_D^{20}$ 1.5498 (Example 1) |
| 2 | Cl | Cl | $-S-C_2H_4N(C_2H_5)_2$ | $n_D^{20}$ 00 1.5616 (Example 2) |
| 3 | Cl | Cl | $-S-C_2H_4\overset{+}{N}(C_2H_5)_2 \ I^{\ominus}$ with CH$_3$ | m.p. 80° (Example 3) |
| 4 | Cl | H | $-OC_3H_6N(CH_3)_2$ | |
| 5 | Cl | CN | $-OC_2H_4N(CH_3)_2$ | |
| 6 | Br | Br | $-OC_2H_4\overset{+}{N}(CH_3)_3 \ Br^{\ominus}$ | |
| 7 | Br | H | $-S-C_2H_4N(C_2H_5)_2$ | |
| 8 | CF$_3$ | H | $-OC_2H_4N(CH_3)_2$ | |
| 9 | CF$_3$ | Cl | $-OC_3H_6NHCH_3$ | |
| 10 | CF$_3$ | H | $-S-C_2H_4-N\text{(piperidine)}$ | |
| 11 | Cl | Cl | $-O-C_2H_4-N\text{(morpholine)}$ | $n_D^{22}$ 1.5652 |
| 12 | Cl | Cl | $-S-C_2H_4-N\text{(pyrrolidine)}$ | |
| 13 | Cl | CN | $-S-C_3H_6-N(CH_3)-CH_2-CH=CH_2$ | |
| 14 | Cl | Cl | $-O-C_2H_4N(CH_2-CH=CH_2)_2$ | $n_D^{22}$ 1.5586 |
| 15 | Cl | H | $-OC_2H_4N(C_2H_4OH)_2$ | |
| 16 | Cl | H | $-OC_2H_4\overset{+}{N}(C_2H_4OH)_2 \ Br^{\ominus}$ with CH$_3$ | |
| 17 | Cl | Cl | $-OC_2H_4-\overset{\oplus}{N}(CH_3)_2-CH_2-CH=CH_2 \ Cl^{\ominus}$ | m.p. 80° (decomp.) |
| 18 | Cl | Cl | $-OC_2H_4-\overset{\oplus}{N}(CH_3)_2-CH_2-\text{C}_6\text{H}_5 \ Cl^{\ominus}$ | m.p. 75° (decomp.) |
| 19 | Cl | Cl | $-OC_2H_4-\overset{\oplus}{N}H\text{(pyrrolidinium)} \ Cl^{\ominus}$ | m.p. 162°–64° |
| 20 | Cl | Cl | $-OC_2H_4-N\text{(piperidine)}$ | $n_D^{21}$ 1.5448 (Example 4) |
| 21 | Cl | Cl | $-OC_2H_4-N(C_2H_5)_2$ | $n_D^{21}$ 1.5415 |
| 22 | Cl | Cl | $-OC_2H_4-N(CH_2-CH_2-OH)_2$ | $n_D^{21}$ 1.5598 |
| 23 | Cl | Cl | $-OC_2H_4-N(CH_3)-\text{C}_6\text{H}_5$ | $n_D^{21}$ 1.5781 |
| 24 | Cl | Cl | $-OC_2H_4-N(CH_3)-CH(CH_3)_2$ | $n_D^{21}$ 1.5501 |
| 25 | Cl | Cl | $-OC_2H_4-N(CH_3)-CH(CH_3)(CH_2)$ | $n_D^{21}$ 1.5572 |

-continued $$X-\overset{Y}{\underset{N}{\bigcirc}}-O-\bigcirc-O-\overset{CH_3}{\underset{|}{CH}}-COZ\text{ alkylene }Q$$

| No. | X | Y | —Z-alkylene Q | Physical constants |
|---|---|---|---|---|
| 26 | Cl | Cl | —OC$_2$H$_4$—N(H)—C$_2$H$_5$ | n$_D^{21}$ 1.5511 |
| 27 | Cl | Cl | —OC$_2$H$_4$—N(H)—CH(CH$_3$)—CH$_2$OCH$_3$ | n$_D^{21}$ 1.5397 |
| 28 | Cl | Cl | —OC$_2$H$_4$—N(H)—CH$_3$ | n$_D^{21}$ 1.5543 |
| 29 | Cl | Cl | —OC$_2$H$_4$—N(H)—CH$_2$—CH=CH$_2$ | n$_D^{21}$ 1.5578 |
| 30 | Cl | Cl | —OC$_2$H$_4$—N(H)—C(CH$_3$)$_2$—CN | |
| 31 | Cl | Cl | —OC$_2$H$_4$—N(H)—C(CH$_3$)$_2$—C≡CH | n$_D^{21}$ 1.5507 |
| 32 | Cl | Cl | —OC$_2$H$_4$—N(CH$_3$)—CH$_2$—COOC$_2$H$_5$ | |
| 22 | Cl | Cl | —OC$_2$H$_4$—N(piperazine)N—CH$_3$ | N$_D^{21}$ 1.5580 |
| 34 | Cl | Cl | —OC$_2$H$_4$—N(H)—C(CH$_3$)$_3$ | n$_D^{21}$ 1.5433 |
| 35 | Cl | Cl | —O—C$_2$H$_4$—$^\oplus$N(pyridinium) Cl$^\ominus$ | n$_D^{21}$ 1.5930 |
| 36 | Cl | Cl | —O—C$_2$H$_4$—$^\oplus$N(pyridinium-4-CH$_3$) Cl$^\ominus$ | |
| 37 | Cl | Cl | —O—C$_2$H$_4$—$^\oplus$N(pyridinium-3-CH$_3$) Cl$^\ominus$ | |
| 38 | Cl | Cl | —O—C$_2$H$_4$—$^\oplus$N(pyridinium-3-C$_2$H$_5$-4-CH$_3$) Cl$^\ominus$ | |

The invention relates also to herbicidal compositions which contain a novel active substance of the formula I, and to processes for the pre-emergence and, in particular, post-emergence combating of weeds, especially monocotyledonous wild grasses.

The compositions according to the invention can be made up in the customary formulations.

The compositions according to the invention are produced in a manner known per se by the intimate mixing and/or grinding of the active substances of the formula I with suitable carriers, optionally with the addition of dispersing agents or solvents which are inert to the active substances. The active substances can be obtained and used in the following forms:

solid preparations: dusts, scattering agents, granules, (coated granule, impregnated granules and homogeneous granules);

liquid preparations:
(a) water-dispersible concentrates of active substance: wettable powders, pastes or emulsions;
(b) solutions.

The production of the compositions according to the invention is illustrated by the following formulation examples.

WETTABLE POWDERS

The following constituents are used to produce (a) a 50%, (b) a 25%, and (c) a 10% wettable powder:

(a) 50 parts of α-[4-(3',5'-dichloropyridyl-2'-oxy)-phenoxy]-propionic acid-dimethylamino-ethyl ester,
   5 parts of sodium dibutyl-naphthalene sulfonate,
   3 parts of naphthalenesulfonic acid/phenolsulfonic acid/formaldehyde condensate (3:2:1),
   20 parts of kaolin, and
   22 parts of Champagne chalk;
(b) 25 parts of the above active substance,
   5 parts of the sodium salt of oleyl methyl tauride,
   2.5 parts of naphthalenesulfonic acid/formaldehyde condensate,
   0.5 part of carboxymethylcellulose,
   5 parts of neutral potassium-aluminium silicate, and
   62 parts of kaolin; and
(c) 10 parts of the above active substance,
   3 parts of a mixture of the sodium salts of saturated fatty alcohols,
   5 parts of naphthalenesulfonic acid/formaldehyde condensate, and
   82 parts of kaolin.

The given active substance is absorbed onto the appropriate carriers (kaolin and chalk), and the material is subsequently mixed and ground. Wettable powders having excellent wetting and suspension properties are obtained. Suspensions of any desired concentration can be obtained from such wettable powders by dilution with water. Suspensions of this kind are used for combating weeds and wild grasses in crops of cultivated plants using the pre-emergence process, and for treating lawns.

PASTE

The following substances are used to produce a 45% paste:
   45 parts of α-[4-(3',5'-dichloropyridyl-2'-oxy)-phenoxy]-thiopropionic acid-S-diethylaminoethyl ester,
   5 parts of sodium aluminium silicate,
   14 parts of cetyl polyethylene glycol ether having 8 mols of ethylene oxide,
   1 part of oleyl polyethylene glycol ether having 5 mols of ethylene oxide,
   2 parts of spindle oil,
   23 parts of water, and
   10 parts of polyethylene glycol.

The active substance is intimately mixed and ground with the additives in apparatus suitable for the purpose. There is obtained a paste from which can be produced, by dilution with water, suspensions of any desired concentration.

EMULSION CONCENTRATE

The following constituents are mixed together to produce a 25% emulsion concentrate:
   25 parts of α-[4-(3',5'-dichloropyridyl-2'-oxy)-phenoxy]-thiopropionic acid-5-diallylaminoethyl ester,
   10 parts of a mixture of nonylphenolpolyoxyethylene and calcium dodecylbenzene sulfonate,
   10 parts of cyclohexanone, and
   55 parts of xylene.

This concentrate can be diluted with water to give emulsions at concentrations suitable for application.

Instead of using the respective active substances given in the preceding formulation examples, it is also possible to use any other of the compounds embraced by the formula I.

Compositions of the invention containing as active ingredient at least one compound of the formula I are suitable in particular for selectively combating difficultly control lable monocotyledonous wild grasses, by pre-emergence and especially post-emergence application, in crops of cultivated plants, for example wheat, but also soya bean, cotton, sugar cane, and so forth.

The following test methods serve to demonstrate the suitability of the compositions according to the invention as herbicides (pre- and post-energence):

PRE-EMERGENCE HERBICIDAL ACTION
(inhibition of germination)

Immediately after sowing the test plants in seed trays in a greenhouse, the surface of the soil is treated with aqueous dispersions of the active substances, which have been prepared from a 25% emulsion concentrate, and from a 25% wettable powder containing acctive substances which cannot be produced as emulsion concentrates owing to inadequate solubility. Four different concentration series are used, corresponding to 4, 2, 1 and 0.5 kg of active substance per hectare. The seed trays are left in the greenhouse at 22°–25° C. with 50–70% relative humidity, and the test is evaluated after 3 weeks, with the results being assessed according to the following scale of ratings:
1 = plants have not germinated or have fully died off,
2–3 = very intense action,
4–6 = moderate action,
7–8 = slight action,
9 = no action (as in the case of untreated control plants)
— = plant not tested with this active-substance concentration.

The following are used as test plants:

| | |
|---|---|
| Hordeum (barley) | Setaria italica |
| Triticum (wheat) | Echinochloa crus galli |
| Zea (maize) | Beta vulgaris |
| Sorghum hybr. (millet) | Sida spinosa |
| Oryza (rice) | Sesbania exaltata |
| Glycine (soya bean) | Amaranthus retroflexus |
| Gossypium (cotton) | Sinapis alba |
| Avena fatua | Ipomoea purpurea |
| Lolium perenne | Galium aparine |
| Alopecurus myosuroides | Pastinaca sativa |
| Bromus tectorum | Rumex sp. |
| Cyperus esculentus | Chrysanthemum leucum |
| Rottboellia exaltata | Abutilon sp. |
| Digitaria sanguinalis | Solanum nigrum |

POST-EMERGENCE HERBICIDAL ACTION
(contact herbicide)

A fairly large number (at least 7) of weeds and of cultivated plants, both monocotyledonous and dicatyledonous, are sprayed after emergence (in the 4- to 6-leaf stage) with an aqueous active-substance dispersion in dosage amounts of 0.06, 0.125, 0.25, 0.5, 1, 2 and 4 kg of active substance per hectare, and the sprayed weeds and cultivated plants are then kept at 24°–26° C. with 45–60% relative humidity. Fifteen days after treatment, the test is evaluated, and the results are assessed according to the same scale of ratings as used in the pre-emergence test.

The selective action of the compounds according to the invention against *Avena fatus* (wild oats) in crops of wheat has been verified by the following test.

Pots are sown with seeds of wheat and of wild oats in a greenhouse. After about 2 weeks, when the plants have emerged and have reached the 3-4 leaf-stage, they are sprayed with diluted aqueous suspension concentrates. The amount of active substance is so proportioned that it is equivalent to an applied amount in the field of ⅛, ¼, ½, 1 or 2 kg per hectare. The pots are then kept in the greenhouse at 24°-26° C. with 45-60% relative humidity. The test is evaluated after 3 weeks according to the above-given scale of values.

The following substances were tested in addition to the compounds according to the invention:

A. α-[4-(4'-trifluoromethylphenoxy)-phenoxy]-propionic acid-dimethylamino-ethyl ester, known from German Offenlegungsschrift No. 2,617,804;

B. α-[4-(4'-trifluoromethylphenoxy)-phenoxy]-propionic acid-2-(trimethylammonium)-ethyl ester iodide, known from German Offenlegungsschrift No. 2,617,804;

C. α-[4-(3',5'-dichloropyridyl-2'-oxy)-phenoxy]-propionic acid-morpholine-amide, known from German Offenlegungsschrift No. 2,546,251; and D. α-[4-(2',4'-dichlorophenoxy)-phenoxy]-propionic acid-2 N-pyrrolidinium-ethyl ester chloride, known from German Offenlegungsschrift No. 2,623,558.

The results are summarised in the Table below:

| Plant | Wild oat (avena fatua) | | | | Wheat | | | |
|---|---|---|---|---|---|---|---|---|
| applied amount in kg/hectare | 2 | 1 | ½ | ¼ | 2 | 1 | ½ | ¼ |
| compound No. | | | | | | | | |
| 1 | 1 | 1 | 1 | 1 | 4 | 8 | 9 | 9 |
| 2 | 1 | 1 | 1 | 1 | 6 | 8 | 9 | 9 |
| 3 | 1 | 1 | 2 | 2 | 9 | 9 | 9 | 9 |
| A | 1 | 1 | 2 | 3 | 1 | 2 | 4 | 5 |
| B | 1 | 1 | 2 | 7 | 1 | 2 | 9 | 9 |

Under these test conditions, the compounds 1, 2 and 3 destroy the wild oat plants but leave the wheat unharmed.

The following results were obtained in a further extended test.

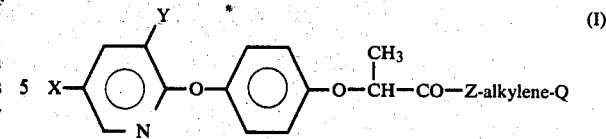

in which
X is a halogen atom or the trifluoromethyl group,
Y is hydrogen, a halogen atom or the trifluoromethyl group,
Z is oxygen or sulfur,
"alkylene" is a straight-chain or branched-chain $C_2$-$C_6$ alkyl group which can be interrupted by oxygen,
Q is an amino or ammonio group

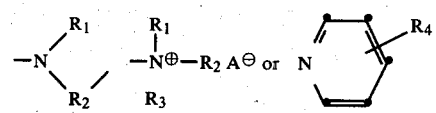

$R_1$ is hydrogen, $C_1$-$C_6$ alkyl unsubstituted or substituted by hydroxyl, halogen, cyano, $CC_1$-$C_4$ alkoxy, carboxyl or $C_1$-$C_4$ alkoxycarbonyl, or it is $C_3$-$C_6$ alkenyl unsubstituted or substituted by halogen, or it is $C_3$-$C_6$ alkynyl,
$R_2$ is the same as $R_1$ or it is phenyl unsubstituted or substituted by halogen, $C_1$-$C_4$ alkyl, $C_1$-$C_4$ alkoxy, $C_1$-$C_4$ alkylthio, cyano, nitro or trifluoromethyl,
$R_1$ and $R_2$ together with the nitrogen atom to which they are bound are also a 5-6-membered heterocycle which can contain as second hetero atom oxygen, sulfur or nitrogen, and can be substituted by $C_1$-$C_4$ alkyl or phenyl,
$R_3$ is the same as $R_1$,
$R_4$ is hydrogen, methyl, ethyl or halogen, and
$A^\ominus$ is the anion of an organic or inorganic acid.

2. The pyridyloxy-phenoxy-α-propionic acid-aminoalkyl ester according to claim 1 of the formula

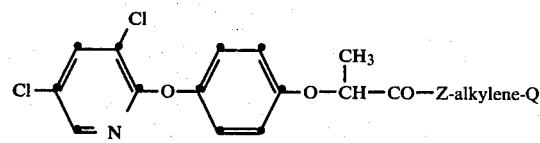

| | Plant | | | | | | | | |
|---|---|---|---|---|---|---|---|---|---|
| Amount applied in kg/hect. | Avena fatua | Lolium perenne | Alopecurus myosuroides | Rottboelia exaltata | Digitaria sanguinalis | Echinochloa crus galli | Wheat | Soya bean | Sugar beet |
| | 1 ½ ¼ ⅛ | 1 ½ ¼ ⅛ | 1 ½ ¼ ⅛ | 1 ½ ¼ ⅛ | 1 ½ ¼ ⅛ | 1 ½ ¼ ⅛ | 1 ½ ¼ ⅛ | 1 ½ ¼ ⅛ | 1 ½ ¼ ⅛ |
| compound No | | | | | | | | | |
| 1 | 1 1 1 3 | 1 2 2 3 | 1 2 2 2 | 1 1 1 1 | 1 1 1 1 | 1 1 1 1 | 8 9 9 9 | 9 9 9 9 | 9 9 9 9 |
| 2 | 1 1 1 2 | 1 2 2 6 | 1 2 3 4 | 1 1 1 1 | 1 1 1 1 | 1 1 1 1 | 8 9 9 9 | 9 9 9 9 | 9 9 9 9 |
| 3 | 1 2 2 3 | 2 3 7 8 | 3 4 4 9 | 1 1 2 4 | 1 2 2 2 | 1 1 1 1 | 9 9 9 9 | 9 9 9 9 | 9 9 9 9 |
| 11 | 1 1 1 2 | 1 1 1 1 | 1 1 1 2 | 1 1 1 1 | 1 1 1 1 | 1 1 1 1 | 1 9 9 9 | 9 9 9 9 | 9 9 9 9 |
| 14 | 1 1 1 2 | 1 1 1 3 | 1 1 1 2 | 1 1 1 1 | 1 1 1 1 | 1 1 1 1 | 3 9 9 9 | 9 9 9 9 | 9 9 9 9 |
| 19 | 1 1 1 6 | 1 1 5 6 | 1 1 1 3 | 1 1 1 2 | 1 1 1 2 | 1 1 1 1 | 7 9 9 9 | 9 9 9 9 | 9 9 9 9 |
| C | 6 9 9 9 | 8 9 9 9 | 7 7 8 8 | 7 9 9 9 | 2 2 6 6 | 1 1 7 9 | 9 9 9 9 | 9 9 9 9 | 9 9 9 9 |
| D | 7 8 9 — | 9 9 9 — | 9 9 9 — | 7 8 9 — | 7 8 8 — | 1 1 2 — | 9 9 9 9 | 9 9 9 9 | 9 9 9 9 |

What is claimed is:

1. A pyridyloxy-phenoxy-α-propionic acid-aminoalkyl ester of the formula I in which Z, "alkylene" and Q are as defined under the formula I.

3. α-[4-(3',5'-Dichloropyridyl-2'-oxy)-phenoxy]-propionic acid-dimethyl-aminoethyl ester.

4. α-[4-(3',5'-Dichloropyridyl-2'-oxy)-phenoxy]-thiopropionic acid-s-diethylaminoethyl ester.

5. α-[4-(3',5'-Dichloropyridyl-2'-oxy)-phenoxy]-propionic acid-2-morpholinoethyl ester iodide.

6. α-[4-(3',5'-Dichloropyridyl-2'-oxy)-phenoxy]-propionic acid-2-diethylaminoethyl ester.

7. A herbicidal composition containing a pyridyloxy-phenoxy-propionic acid-aminoalkyl ester of the formula I, claim 1, as active ingredient.

8. A method for controlling monocotyledonous weeds, which comprises applying to an area where such weeds prevail an effective amount of a pyridyloxy-phenoxy-propionic acid aminoalkyl ester of the formula I, claim 1 or of a composition containing same.

9. A method for selectively controlling monocotyledonous weeds in crops of cultivated plants, which comprises applying to such crop areas an effective amount of a pyridyloxy-phenoxy-propionic acid aminoalkyl ester of formula I, claim 1 or of a composition containing same.

10. A method for selectively controlling the weed avena fatua in crops of cereal, which comprises applying to such crop areas an effective amount of a pyridyloxy-phenoxy-propionic acid aminoalkyl ester of formula I, claim 1 of a composition containing same.

* * * * *